United States Patent [19]
Miller et al.

[11] Patent Number: 4,524,764
[45] Date of Patent: Jun. 25, 1985

[54] KNEE BRACE

[76] Inventors: Harold E. Miller, R.R. 1, Box 185, West Branch, Iowa 52358; Ronald W. Cheney, 2004 Center St., West Des Moines, Iowa 50265

[21] Appl. No.: 529,261

[22] Filed: Sep. 6, 1983

[51] Int. Cl.³ ............................................. A61F 3/00
[52] U.S. Cl. .................................... 128/80 C; 128/88
[58] Field of Search ..................... 128/80 C, 80 F, 88; 3/23; 16/354; 403/92, 93, 97

[56] References Cited

U.S. PATENT DOCUMENTS

| | | | |
|---|---|---|---|
| 50,770 | 10/1865 | Lockwood | 3/23 |
| 2,072,028 | 2/1937 | Cooper | 16/354 |
| 4,323,059 | 4/1982 | Rambert et al. | 128/80 C |
| 4,372,298 | 2/1983 | Lerman | 128/80 C |

Primary Examiner—John D. Yasko
Attorney, Agent, or Firm—Zarley, McKee, Thomte, Voorhees & Sease

[57] ABSTRACT

The knee brace of the present invention comprises a pair of elongated articulated assemblies adapted to embrace the interior and exterior surfaces of the knee. Each assembly comprises an upper member, a lower member, and a hinge pivotally interconnecting the upper and lower members. The upper and lower members each include arcuate gear surfaces which intermesh during articulated movement of the members and the hinge. The gear surfaces include annular flanges which reinforce the gear teeth on the gear surfaces.

8 Claims, 7 Drawing Figures

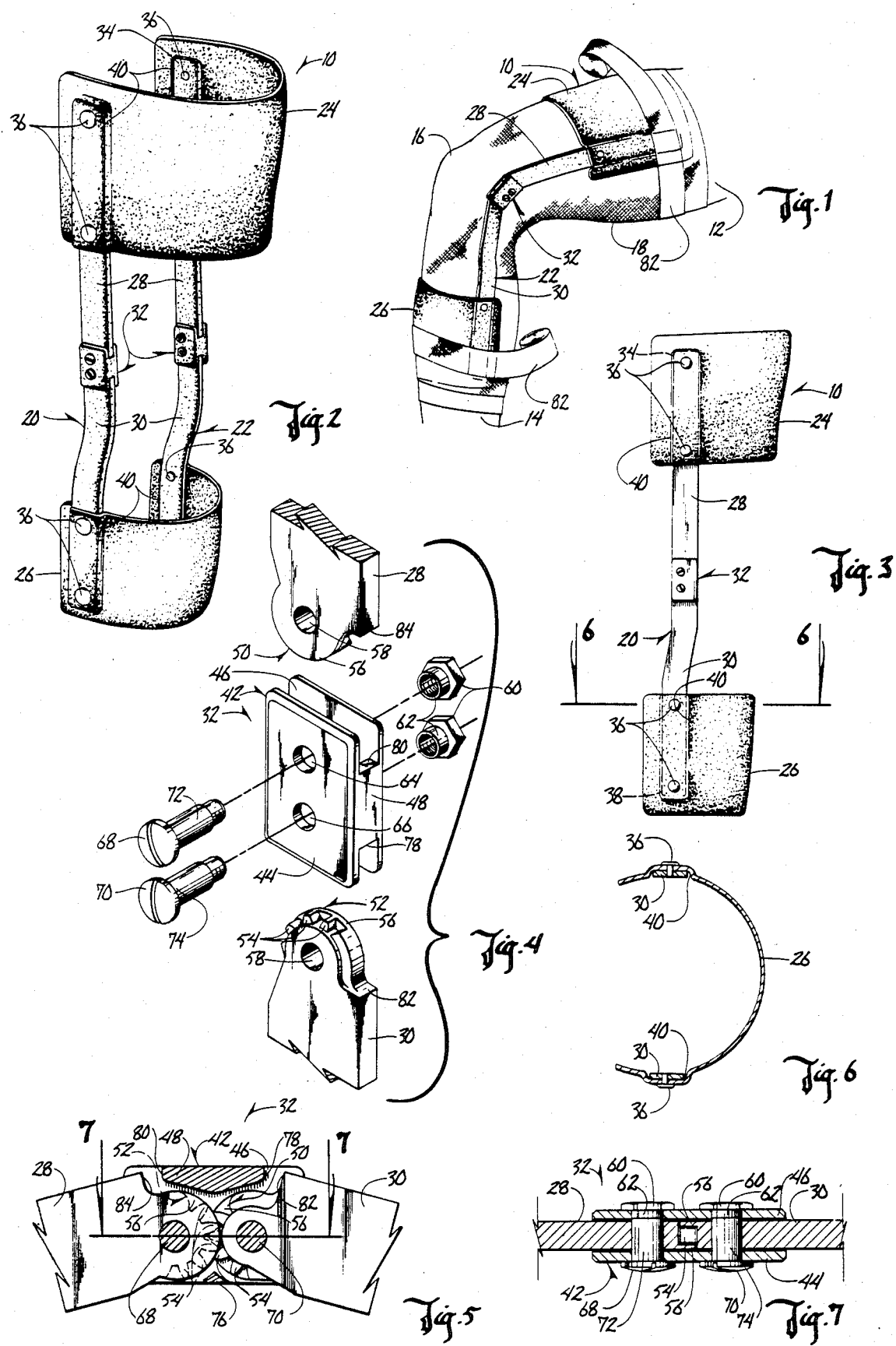

KNEE BRACE

BACKGROUND OF THE INVENTION

This invention relates to a knee brace.

One of the most vulnerable areas of the body to injury in athletics is the knee. Many serious injuries which occur to the knee are the result of hyper-extension of the knee, that is, the articulation of the knee beyond a point normally permitted by the knee joint. Another major cause of knee injuries results from unnatural medial (inward) and lateral (outward) movement of the knee joint. Often both of these types of injuries result in tearing of ligaments and other knee parts so that the athlete is disabled for a considerable length of time.

Various types of devices have been developed in an attempt to protect the knee against unnatural medial-lateral movement and hyper-extension. However, most of these devices are heavy and cumbersome, and severely restrict the ability of the athlete to perform. Furthermore, many of these devices do not provide sufficient positive support for the knee to prevent injury to the knee.

One type of prior knee brace which has been used includes an articulated hinge joint having intermeshing teeth. The teeth are provided on the adjacent ends of two hinged members and interlock during pivotal movement of the two hinged members with respect to one another. A hinge strap interconnects the two members and holds the teeth in interlocking relationship.

This type of knee brace has been found defective because the teeth sometimes break, bend, or shear when exposed to the rigors of the athlete's movements.

Therefore, a primary object of the present invention is the provision of an improved knee brace.

A further object of the present invention is the provision of a knee brace which uses interlocking gear teeth at the pivot joint and which includes means for preventing the shearing, bending or cutting of the teeth in response to outside forces.

A further object of the present invention is the provision of an improved knee brace which is lightweight and which does not affect the performance of the athlete.

A further object of the present invention is the provision of a knee brace which permits free and easy movement of the knee joint throughout the range of natural articulation, but which at the same time provides at least some protection against hyper-extension of the knee beyond a point of natural articulation.

A further object of the present invention is the provision of a knee brace which protects against unnatural medial-lateral movement of the knee joint.

A further object of the present invention is the provision of a device which is easy and simple to apply to the knee so that it can be put on and removed with ease.

A further object of the present invention is the provision of a device which is comfortable to the athlete and does not affect his natural movements.

A further object of the present invention is the provision of a device which has a minimum of bulk so that it can fit easily under clothing or uniforms.

A further object of the present invention is the provision of a device which will withstand severe collisions and trauma during contact sports.

A further object of the present invention is the provision of a device which is economical to manufacture, durable in use and efficient in operation.

SUMMARY OF THE INVENTION

The present invention contemplates two articulated assemblies, each of which include an upper member and a lower member joined by a hinge therebetween. The assemblies are preferably constructed of plastic such as Nylon (a trademark of DuPont Company), so that they will have a maximum amount of strength while at the same time having a minimum amount of weight.

The adjacent ends of the upper and lower members each are provided with a planetary gear surface having gear teeth and having an annular flange positioned at one side of the gear teeth. This annular flange strengthens the teeth and reinforces them against bending, breaking, or shearing.

A pair of stop shoulders on the hinge limit the articulated movement of the assemblies beyond a predetermined point which corresponds to the maximum desired articulation of the knee. The hinge permits free pivotal movement of the links up to this predetermined angle.

The articulated assemblies are secured to the knee by conventional wraps or tape which is wound around the leg of the athlete with the articulated members positioned on the interior and exterior surfaces of the knee.

The two assemblies may be interconnected by an upper arcuate sheet which interconnects the two upper members and a lower arcuate sheet which interconnects the two lower members. These arcuate sheets conform to the shape of the athlete's leg, and engage the anterior surface of the patient's upper and lower legs when the stop means are engaged.

The hinge used with the present invention comprises a short link or strap which has two pins extending therethrough. One of the pins also extends through the lower end of the upper member of the articulated assembly, and the other pin extends through the upper end of the lower member of the articulated assembly. The upper and lower ends of the articulated assembly each are provided with cogs or gears which intermesh and which have annular flanges associated with them, so as to provide added reinforcement to the hinge assembly.

The present invention is made of plastic, preferably Nylon, which is light in weight. The dimensions of the articulated assemblies also contribute to the minimum amount of weight provided by the devices. The upper and lower members are approximately one inch wide, and because of this small dimension they do not interfere with the freedom of movement of the knee joint when the device is applied.

The device permits the knee to move freely throughout the normal range of articulation of the knee joint. However, the hinge joint resists unnatural medial-lateral movement of the knee so as to prevent injury. In the event that the knee joint is urged to a hyper-extended position, the knee brace of the present invention by virtue of the stop on the hinge means, limits the movement of the knee so as to minimize the possibility that the knee will become hyper-extended. It has been found that this device works satisfactorily even in contact sports such as football, where the joint is subjected to forces of great magnitude.

BRIEF DESCRIPTION OF THE FIGURES OF THE DRAWINGS

FIG. 1 is a perspective view of a knee joint showing the knee brace in place thereon.

FIG. 2 is a perspective view of the knee brace.

FIG. 3 is a side elevational view of the knee brace.

FIG. 4 is a perspective view showing the hinge joint of the knee brace in exploded fashion.

FIG. 5 is a partial sectional view of the hinge joint of the knee brace.

FIG. 6 is a sectional view taken along line 6—6 of FIG. 3.

FIG. 7 is a sectional view taken along line 7—7 of FIG. 5.

DETAILED DESCRIPTION OF THE PREFERRED EMBODIMENT

Referring to the drawings, the numeral 10 generally refers to the knee brace of the present invention. In FIG. 1, knee brace 10 is shown mounted on an athlete's knee joint which for purposes of reference includes an upper leg portion 12, a lower leg portion 14, and a knee 16. Also for purposes of reference, the forward portion of the athlete's leg is referred to as the anterior portion, the rearward portion is referred to as the posterior portion, the inside of the knee is referred to as the medial portion, and the lateral outside of the knee is referred to as the lateral portion. Wrapped around the knee underneath device 10 is a conventional knee wrap or bandage 18, which provides a cushion between the knee brace 10 and the skin of the athlete's leg. The knee wrap or bandage 18 also further provides reinforcement to the joint.

Referring to FIGS. 2 and 3, the knee brace 10 of the present invention comprises a pair of spaced apart articulated assemblies 20, 22 which are joined together by virtue of semicircular sleeves 24, 26. Each articulated assembly 20, 22 comprises an upper member 28, a lower member 30, and a hinge mechanism 32 pivotally interconnecting upper and lower members 28, 30. Upper members 28 each include an upper end 34, which is secured by means of rivets 36 to sleeve 24. Similarly, lower members 30 each include a lower end 38 which is secured by means of rivets 36 to sleeve 26. Referring to FIG. 6, sleeve 26 is shown to have a deformed channel 40 which is sized to receive the lower ends 38 of lower members 30 so as to prevent the members 30 from protruding inwardly beyond the inner curved surface of sleeve 26. This provides a smooth surface which does not irritate or cause pain to the athlete's leg when the sleeve 26 is fitted thereagainst. Sleeve 24 also includes similar channels 40 for receiving the upper ends 34 of upper members 28.

Referring to FIGS. 4, 5 and 7, hinge mechanism 32 comprises a link or strap 42 having a pair of spaced apart strap plates 44, 46 which are held apart by a web 48. Upper member 28 includes a partial planetary gear surface 50 at its lower end, and lower member 20 includes a partial planetary gear surface 52 at its upper end. Gear surfaces 50, 52 each include a plurality of gear teeth 54, a side flange 56, and a pivot hole 58 located at the center of curvature of gear surface 50. It should be noted that gear surfaces 50, 52, while symmetrical, are complementary to one another so that when they mesh together the flanges 56 are positioned outwardly.

A pair of nuts 60, each of which includes a bushing 62, are fitted within a pair of spaced apart apertures 64, 66 extending through strap plates 44, 46. A pair of shouldered bolts 68, 70 extend through holes 64, 66 and also extend through holes 58 of gear surfaces 50, 52 respectively. Bolts 68, 70 are then threaded within nuts 60 so as to provide securement of the upper and lower members to the hinge mechanisms 32. Bolts 68, 70 include bushing surfaces 72, 74 which permit the upper leg 28 and the lower leg 30 to pivot thereabout.

FIGS. 5 and 7 illustrate the manner in which the gear surfaces 50, 52 intermesh when they are assembled within hinge mechanism 52. Flanges 58 are positioned on the outside of the intermeshing gear assemblies, and gear teeth 54 intermesh with one another. Because the circular surface of the gear surfaces 50, 52 are concentric with the pins 68, 70, the two members 28, 30 are free to pivot with respect to one another, with the gear teeth 54 remaining in constant intermeshing relationship. The flanges 58 provide further stability to the joint so that it will have stability in response to outside forces from any direction. Furthermore, flanges 58 provide added strength to teeth 54 so as to increase their ability to resist bending, breaking or shearing.

A small interconnecting member 76 interconnects strap plates 44, 46 on the side opposite from web 48. Web 48 is provided with two axially facing shoulders 78, 80. Upper leg member 28 is provided with a complementary shoulder 82 adapted to engage shoulder 78, and lower leg member 30 is provided with a complementary shoulder 84 adapted to engage shoulder 80. As can be seen in FIG. 5, shoulders 78, 80, 82, and 84 prevent upper and lower members 28, 30 from pivoting beyond approximately 180° with respect to one another. However, in the opposite direction, the legs 28, 30 are free to pivot in the opposite direction as far as the human knee is likely to bend.

When the device is mounted on an athlete's knee as shown in FIG. 1, the shoulders 78, 80, 82, 84 are engaged prior to the time that the athlete's knee becomes hyper-extended beyond its natural range of movement. A wrapping, or tape 82, is wrapped around the outside of sleeves 24, 26, and around the athlete's leg so as to secure the knee brace 10 to the athlete's leg in such a fashion that the knee brace and the leg will articulate in unison with respect to one another. When the athlete's leg experiences a tendency to hyper-extend, the shoulders 78, 80 and 82, 84 engage and restrict the articulated movement of the leg beyond a predetermined point.

The device also resists forces in a medial or lateral direction. This resistance is enhanced by the combined effect of the straps 44, 46, the intermeshing teeth 54, and the flanges 58, as well as the other components of the brace.

The device of the present invention can be manufactured from any material which has substantial strength. It could be constructed of metal or plastic. However, in order to minimize the weight while at the same time maximizing the strength of the device, it is preferred that the device be constructed from a plastic material sold by DuPont Company under the trademark Nylon, Product No. ST-801. This material has very good strength, and is lightweight.

It has been found that the device will provide satisfactory reinforcement to the knee even when the upper and lower members 28, 30 are only an inch wide, and approximately one-fourth of an inch thick. Because these smaller dimensions can be used, the device minimizes any interference with the natural movement of the athlete's leg. It has been found that the wearing of the knee brace does not substantially hinder the speed at which an athlete can run, nor the agility with which an athlete can move laterally or up and down. The only substantial restriction which the device provides to the athlete's movement is when the athlete's knee joint is urged to a medial-lateral movement or to a hyper-extended movement.

The device is simple to manufacture, and is quickly and easily applied to the athlete's knee joint. No expertise is required to apply the device. Furthermore, the device is thin and does not obstruct the athlete's clothing or the movement of the athlete's knee joint.

Thus, it can be seen that the device accomplishes at least all of its stated objectives.

What is claimed is:

1. A knee brace for supporting a human leg having a knee, an upper leg portion above said knee, and a lower leg portion below said knee; said knee and said upper and lower leg portions each having an anterior surface, a posterior surface, a medial surface, and a lateral surface, said brace comprising:

a medial articulated assembly and a lateral articulated assembly adapted to embrace said medial and lateral surfaces of said knee therebetween;

each of said articulated assemblies comprising an upper member having upper and lower ends, a lower member having upper and lower ends, and hinge means pivotally interconnecting said upper end of said lower member to said lower end of said upper member;

each of said hinge means comprising a pair of spaced apart strap plates held in rigid spaced apart relation to one another by web means;

said upper ends of said lower members and said lower ends of said upper members extending between and being embraced by said spaced apart strap plates;

each of said hinge means including a pair of spaced apart hinge pins extending through said spaced apart strap plates, one of said pins extending through said lower end of said upper member and the other of said hinge pins extending through said upper end of said lower member to provide first and second hinged axes for said upper and lower members respectively;

said lower ends of said upper members and said upper ends of said lower members each being provided with an arcuate gear surface concentric to said first and second hinge axes respectively, said gear surfaces each including gear teeth and flange means formed adjacent said gear teeth;

said gear teeth of said lower members intermeshing with said gear teeth of said upper members between said spaced apart strap plates whereby said intermeshing gear teeth, said flange means, said hinge pins, said spaced apart strap plates, and said web means combine to resist breaking of said hinge means in response to outside impact forces being applied to said knee.

2. A knee brace according to claim 1 wherein said flange means comprise a lateral flange on one side of the gear teeth, the other side of said gear teeth being open.

3. A knee brace according to claim 1 wherein said hinge means further comprises an interconnecting member spaced from said web means and rigidly interconnecting said spaced apart strap plates.

4. A knee brace according to claim 3 wherein said intermeshing teeth of said upper and lower members are positioned between said web means and said interconnecting member.

5. A knee brace according to claim 1 wherein said web includes stop means thereon for engaging said upper and lower members to limit articulated pivotal movement of said upper and lower members in a first direction beyond a predetermined angle with respect to one another.

6. A knee brace according to claim 5 wherein said stop means comprises a pair of shoulders on said hinge means, said upper and lower members each having a shoulder adapted to engage one of said shoulders on said hinge means to stop pivotal movement of said upper and lower members with respect to one another.

7. A knee brace according to claim 1 wherein said hinge means of said medial articulated assembly is spaced from said hinge means of said lateral articulated assembly, so as to provide an open space therebetween for said human knee, said open space being free from means interconnecting said medial and lateral hinge means so as to permit unobstructed natural movement of said human knee.

8. A knee brace according to claim 7 wherein first connecting means interconnect said upper members of said medial and lateral assemblies at a point spaced above said hinge means and second connecting means interconnect said lower members at a point spaced below said hinge means so as to hold said medial and lateral assemblies in spaced apart relation for embracing the medial and lateral sides of said knee.

* * * * *